US005929042A

United States Patent [19]
Troy et al.

[11] Patent Number: 5,929,042
[45] Date of Patent: Jul. 27, 1999

[54] ANTISENSE COMPOUNDS WHICH PREVENT CELL DEATH AND USES THEREOF

[75] Inventors: Carol M. Troy, Hastings-on-Hudson; Michael L. Shelanski, Brooklyn, both of N.Y.

[73] Assignee: The Trustees of Columbia University in the City of New York, New York, N.Y.

[21] Appl. No.: 08/810,540

[22] Filed: Mar. 3, 1997

[51] Int. Cl.$^6$ ..................................................... A01N 43/04
[52] U.S. Cl. ........................... 514/44; 435/352; 435/366; 536/245
[58] Field of Search .................................. 514/44; 435/6, 435/172.3, 69.1, 352, 366; 536/24.5

[56] References Cited

FOREIGN PATENT DOCUMENTS

WO 95/00160   1/1995   WIPO .
WO 96/00297   1/1996   WIPO .

OTHER PUBLICATIONS

Dorn et al. Pharmacology and Therapeutics, vol. 61, No. 1/2, pp. 155–184 1994.
Prochiantz, A. Current Opinion in Neurobiology. vol. 6, No. 5, pp. 629–634 1996.
Farinelli SE, Park DS, Greene LA (1996) Nitric oxide delays the death of trophic factor–deprived PC12 cells and sympathetic neurons by a cGMP–mediated mechanism. J. Neurosci. 16:2325–2334 (Exhibit 2).
Fernandes–Alnemri T, Litwack G, Alnemri ES (1994) CPP32, a novel human apoptotic protein with homology to Caenorhabditis elegans cell death protein ced–3 and the mammalian IL–1β–converting enzyme J. Biol. Chem. 269:30761–30764 (Exhibit 3).
Farrari G, Yan CYI, Greene LA (1995) N–acetylcysteine (D– and L–stereoisomers) prevents apoptotic death of neuronal cells. J. Neurosci 15:2857–2866 (Exhibit 4).
Gagliardini V, Fernandez P–A, Lee RKK, Drexler HCA, Rotello RJ, Fishman MC, Yuan J. (1994) Prevention of vertebrate neuronal death by the crmA gene. Science 263:826–828 (Exhibit 5).
Greene LA (1978) Nerve growth factor prevents the death and stimulates the neuronal differentiation of clonal PC12 pheochromocytoma cells in serum–free medium. J Cell Biol 78:747–755 (Exhibit 6).
Hengartner MO, Ellis RE, Horvitz HR (1992) Caenorhabditis elegans gene ced–9 protects cells from programmed cell death. Nature. 356: 494–9 (Exhibit 7).
Kumar S (1995) Inhibition of apoptosis by the expression of antisense Nedd2. FEBS Letters 368:69–72 (Exhibit 8).
Kumar S, Knioshita M, Noda M, Copeland NG, Jenkins NA (1994) Induction of apoptosis by the mouse Nedd2 gene, which encodes a protein similar to the product of the Caenorhabditis elegans cell death gene ced–3 and the mammalian IL–1β–converting enzyme. Genes & Develop 8:1613–1626 (Exhibit 9).

Lindenboim L, Haviv R, Stein R (1995) Inhibition of drug–induced apoptosis by survival factors in PC12 cells. J. Neurochem 64:1054–1063 (Exhibit 10).
Miura M, Zhu H, Rotello R, Hartweig EA, Yuan J (1994) Induction of apoptosis in fibroblasts by IL–1β–converting enzyme, a mammalian homolog of the c. elegans cell death gene ced–3. Cell 75:653–660 (Exhibit 11).
Srinivasan A, Foster LM, Testa M–P, Ord T, Keane RW, Bredesan DE, Kayalar, C (1996) Bcl–2 expression in neural cells blocks activation of ICE/CED–3 family proteases during apoptosis. J Neurosci 16: 5654–5660 (Exhibit 12).
Troy CM, Brown K, Greene LA, and Shelanski ML (1990). Ontogeny of the neuronal intermediate filament protein, peripherin, in the mouse embryo. Neurosci. 36: 217–237 (Exhibit 13).
Troy CM, Derossi D, Prochiantz A, Greene LA, Shelanski ML (1996a) Down–regulation of SOD1 leads to cell death by the NO–peroxynitrate pathway. J. Neurosci 16:253–261 (Exhibit 14).
Troy CM, Greene LA, Shelanski ML (1992). Neurite outgrowth in peripherin–depleted PC12 cells. J Cell Biol 117:1085–1092 (Exhibit 15).
Troy CM, Shelanski ML (1994) Down–regulation of copper/zinc superoxide dismutase (SOD1) causes apoptotic death in PC12 neuronal cells. Proc. Natl. Acad. Sci. USA 91:6384–6387 (Exhibit 16).
Troy CM, Stefanis L, Prochiantz A, Greene LA, Shelanski ML (1996b) The contrasting roles of ICE–family proteases and interleukin–1β in apoptosis induced by trophic factor withdrawal and by SOD1 downregulation. Proc Natl Acad Sci USA 93: 5635–5640 (Exhibit 17).

(List continued on next page.)

*Primary Examiner*—James Ketter
*Assistant Examiner*—Irem Yucel
*Attorney, Agent, or Firm*—John P. White; Cooper & Dunham LLP

[57] ABSTRACT

The present invention provides for an antisense oligonucleotide having the sequence 5'GCTCGGCGCCGCCATTTCCAG3'(SEQ ID NO:1). The invention also provides for an antisense oligonucleotide having the sequence 5'GTCAGCGGCCATCAGCTT3'(SEQ ID NO:2). The present invention further provides for a method for treating a neurodegenerative disorder in a subject which comprises administering to the subject a compound in an amount effective to inhibit neuronal cell death and thus treat the neurodegenerative disorder in the subject, which compound comprises the oligonucleotide 5'GCTCGGCGC-CGCCATTTCCAG3' (SEQ ID NO:1) and a delivery agent. The present invention provides for a method of inhibiting trophic factor withdrawal mediated death of a cell which comprises contacting the cell with an amount of the oligonucleotide 5'GCTCGGCGCCGCCATTTCCAG3' (SEQ ID NO:1) effective to inhibit death of the cell.

18 Claims, 10 Drawing Sheets

OTHER PUBLICATIONS

Troy CM, Stefanis L, Greene L A, Shelanski ML (1996c) Mechanisms of neuronal degeneration: a final common pathway? in Neuronal Regeneration, Reorganization and Repair F. Seil, ed. (New York, NY: Raven Press), pp. 103–112 (Exhibit 18).

Wang L, Miura M, Bergeron L, Zhu H, Yuan J (1994) Ich–1, an Ice/ced–3–related gene, encodes both positive and negative regulators of programmed cell death. Cell 78: 739–750 (Exhibit 19).

Yamin, Ting–Ting et al. (1996) "Activation of the Native 45–kDa Precursor Form of Interleukin–1–converting Enzyme," J. Biol. Chem. 271(22): 13273–13282 (Exhibit 20).

Yuan J, Shahan S, Ledoux S, Ellis HM, Horvitz HR (1993) The c. elegans cell death gene ced–3 encodes a protein similar to mammalian interleukin–1β–converting enzyme. Cell 74: 641–652 (Exhibit 21).

FIG. 1A
Control
FIG. 1B
V-ANedd treated
Naive PC12 cells
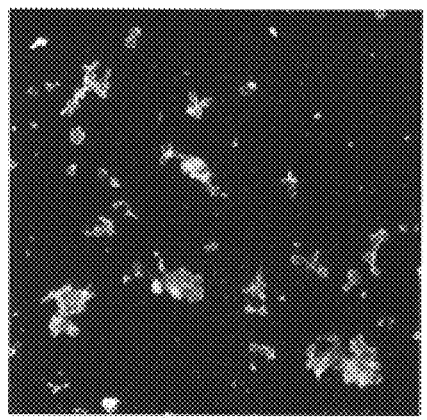
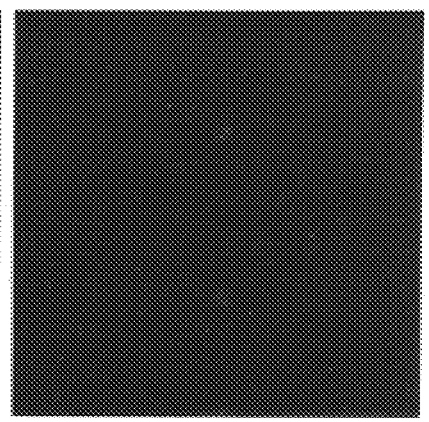
Neuronal PC12 cells
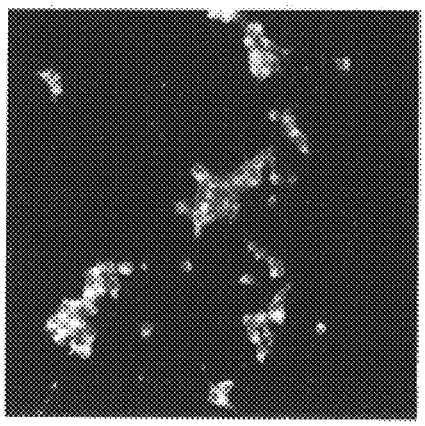
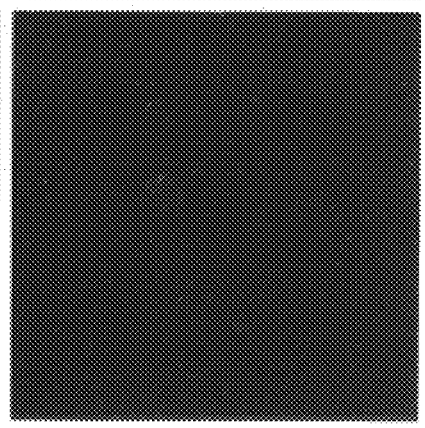
FIG. 1C
FIG. 1D FIG. 2A +NGF
FIG. 2B −NGF
Naive PC12 cells
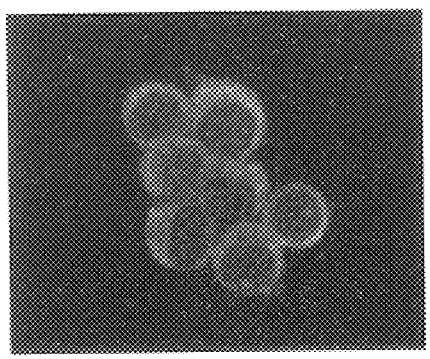
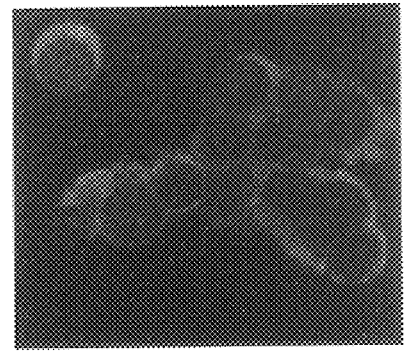
Neuronal PC12 cells
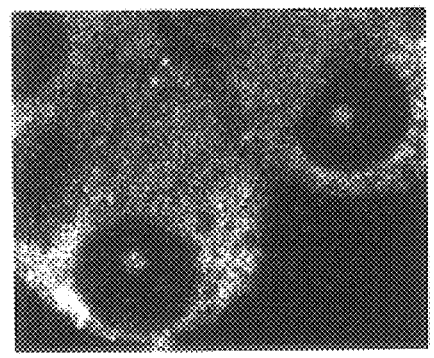
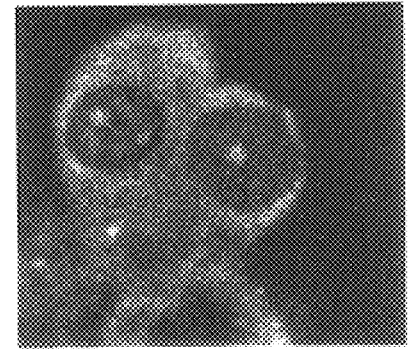
FIG. 2C
FIG. 2D FIG. 3A
FIG. 3B
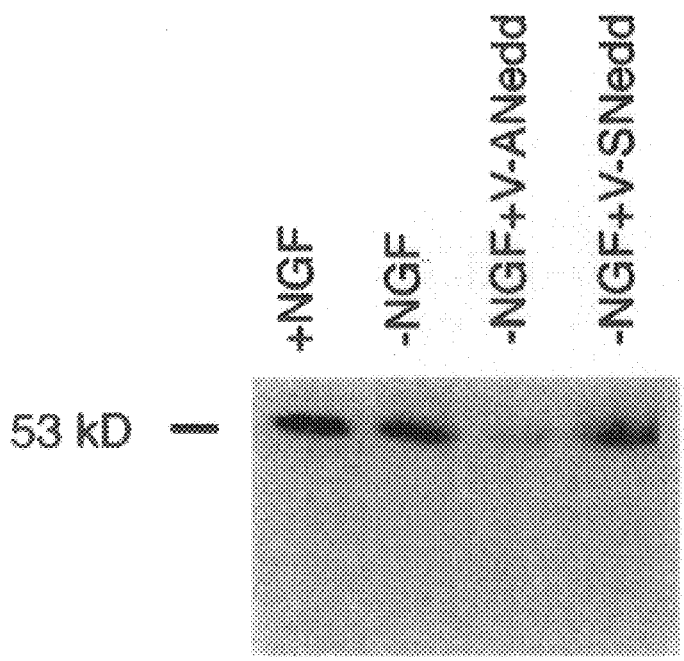
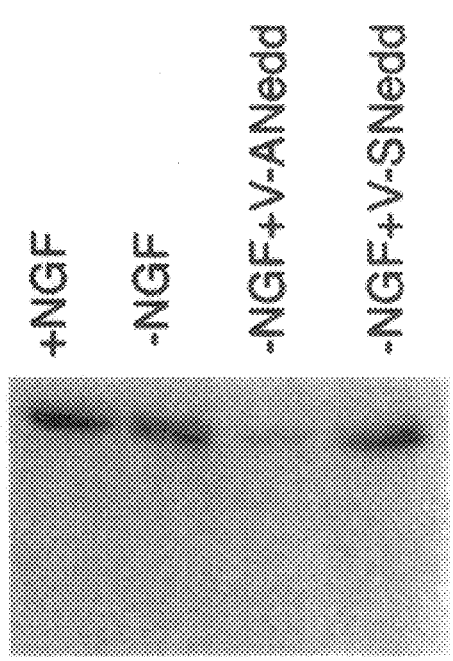

DAYS AFTER NGF WITHDRAWAL

DAYS AFTER TREATMENT

FIG. 7A +NGF
FIG. 7B −NGF
FIG. 7C −NGF +V-ANedd
Naive PC12 cells
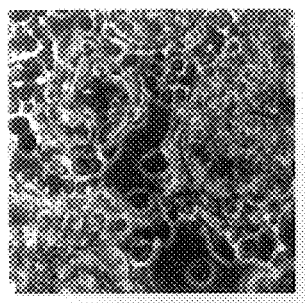 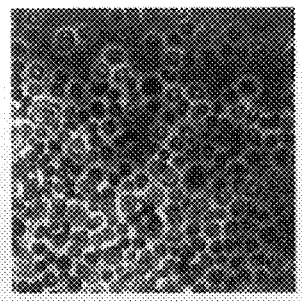 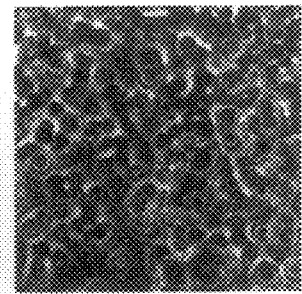
Neuronal PC12 cells
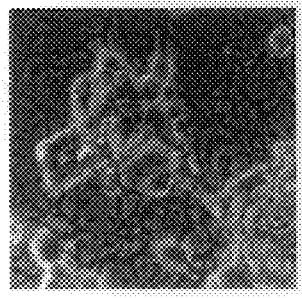 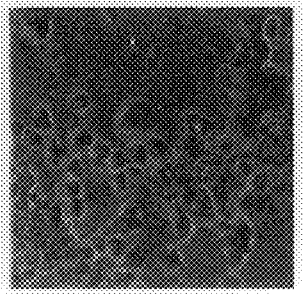 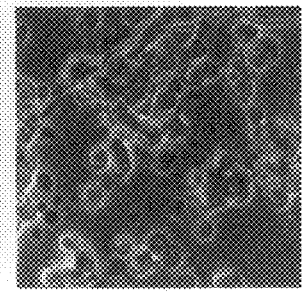
FIG. 7D FIG. 7E FIG. 7F FIG. 7G  
+NGF
FIG. 7H  
-NGF
FIG. 7I  
-NGF  
+V-ANedd
SCG neurons
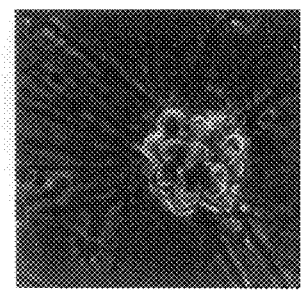
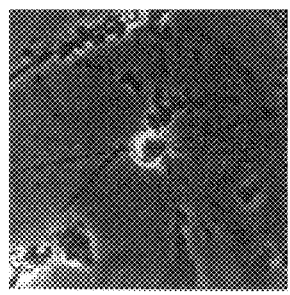
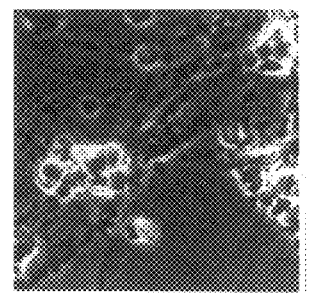

ANTISENSE COMPOUNDS WHICH PREVENT CELL DEATH AND USES THEREOF

The invention disclosed herein was made with Government support under NIH Grants No. and NS15076 from the Department of Health and Human Services. Accordingly, the U.S. Government has certain rights in this invention.

BACKGROUND OF THE INVENTION

Throughout this application, various publications are referenced by author and date. Full citations for these publications may be found listed alphabetically at the end of the specification immediately preceding the claims. The disclosures of these publications in their entireties are hereby incorporated by reference into this application in order to more fully describe the state of the art as known to those skilled therein as of the date of the invention described and claimed herein.

Neuronal death by apoptosis is a normal feature of development in which it appears that the death program is triggered by the failure of a given neuron to compete for limiting supplies of target-derived neurotrophic factors. Neurons also undergo apoptotic death in the post-developmental period when deprived of appropriate trophic factors or when subjected to any of a variety of stresses and injuries. Apoptosis also accounts for at least a portion of cellular loss in degenerative neurological diseases including Alzheimer's disease and amyotrophic lateral sclerosis (Coyle and Puttfarcken, 1993; Schapira, 1995; Williams, 1995; Brown, 1995).

Neuronal apoptotic death may be precipitated by widely different initiating causes. In the rat pheochromocytoma PC12 line, a commonly used model for neuronal differentiation and cell death, apoptosis may be triggered by either trophic factor/NGF withdrawal as well as by sympathetic neurons (Greene, 1978; Rukenstein et al., 1991; Mesner et al., 1992; Pittman et al., 1993; Lindenboim et al., 1995 Batistatou and Greene, 1991) or oxidative stress induced by down-regulation of Cu++/Zn++ superoxide dismutase (SOD1) (Troy and Shelanski, 1994; Troy et al., 1996a,b,c). The initiating mechanisms of death appear to be distinct in each instance. Apoptosis triggered by nerve growth factor (NGF) deprivation is blocked by cAMP analogs (Rydel and Greene, 1988; Rukenstein et al., 1991) and high concentrations of N-acetyl cysteine (Ferrari et al., 1995) whereas these agents do not inhibit death induced by down regulation of superoxide dismutase (SOD1) (Troy et al., 1996 a,c). In contrast, the latter is blocked by vitamin E (Troy and Shelanski, 1994) and inhibitors of nitric oxide (NO) synthase (Troy et al. 1996a), which have no effect on apoptosis evoked by NGF withdrawal (Ferrari et al., 1995; Farinelli et al., 1996). Despite these initial mechanistic differences, there is evidence for common or similar downstream elements in the pathways that lead to death in both paradigms.

SUMMARY OF THE INVENTION

The present invention provides for an antisense oligonucleotide having the sequence 5'GCTCGGCGCCGC-CATTTCCAG3' (Sequence I.D. No. 1). The invention also provides for an antisense oligonucleotide having the sequence 5' GTCAGCGGCCATCAGCTT3' Sequence I.D. No. 2. The present invention further provides for a method for treating a neurodegenerative disorder in a subject which comprises administering to the subject a compound in an amount effective to inhibit neuronal cell death and thus treat the neurodegenerative disorder in the subject, which compound comprises the oligonucleotide 5'GCTCGGCGC-CGCCATTTCCAG3' and a delivery agent. The present invention provides for a method of inhibiting trophic factor withdrawal mediated death of a cell which comprises contacting the cell with an amount of the oligonucleotide 5'GCTCGGCGCCGCCATTTCCAG3' Sequence I.D. No. 1 effective to inhibit death of the cell.

BRIEF DESCRIPTION OF THE FIGURES

FIGS. 1A, 1B, 1C and 1D. Down-regulation of Nedd2 in PC12 cells by Penetratini-linked antisense oligonucleotide to Nedd2 (V-ANedd).

Naive and neuronally differentiated PC12 cells (pretreated for at least 7 days with NGF, nerve growth factor) were plated on Matrigel coated multichamber slides. V-ANedd (400 nM) was added to the indicated cultures after plating. Naive cultures were grown in RPMI 1640 medium with 5% FCS and 10% horse serum; neuronal cultures were grown in RPMI 1640 medium with 1% horse serum and NGF (100 ng/ml). After overnight maintenance, cells were fixed in ice cold methanol and then immunostained with anti-N-Nedd. Cells were observed with a Nikon® fluorescence microscope. x120.

FIGS. 2A, 2B, 2C and 2D. Cellular localization of Nedd2 before and after trophic factor deprivation.

Naive and neuronally differentiated were grown with serum and serum and NGF respectively. The cells were then plated in serum-free RPMI 1640 medium for 20 hrs. with or without NGF as indicated. Cultures were stained with anti-N-Nedd and were observed with a BioRad® MRC600 confocal microscope. x1600.

FIGS. 3A, 3B. Regulation of Nedd2 by V-ANedd.

Naive PC12 cells were grown for 24 hours in serum-free RPMI 1640 medium in the presence or absence of NGF (100 ng/ml) and with or without V-ANedd (400 nM) or V-SNedd (400 nM) as indicated. The cells were extracted in sample buffer, the extracts boiled and equal amounts of protein resolved by 10% SDS-PAGE and transferred to nitrocellulose. Blots were probed with (FIG. 3A) anti-N-Nedd at 1:500 or (FIG. 3B) anti-C-Nedd at 1:330 and staining visualized with ECL. Bands were quantified using Scion Image® software and normalized against peripherin levels. The level of down-regulation is representative of that obtained in 5 independent experiments.

Figure 4A:
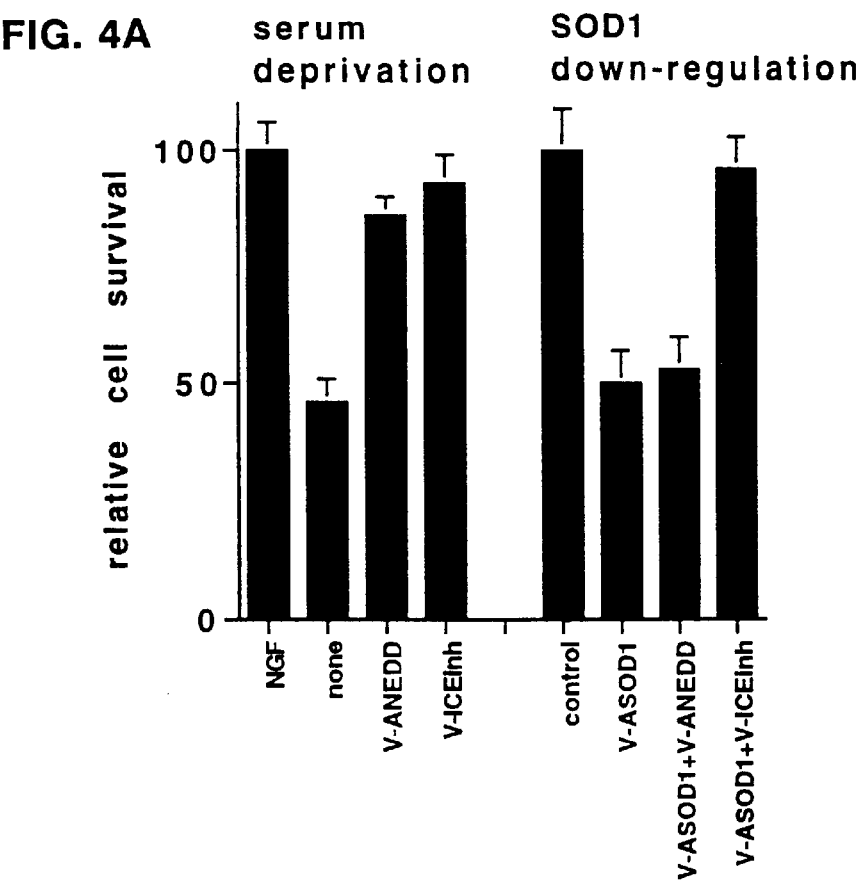
Figure 4B:
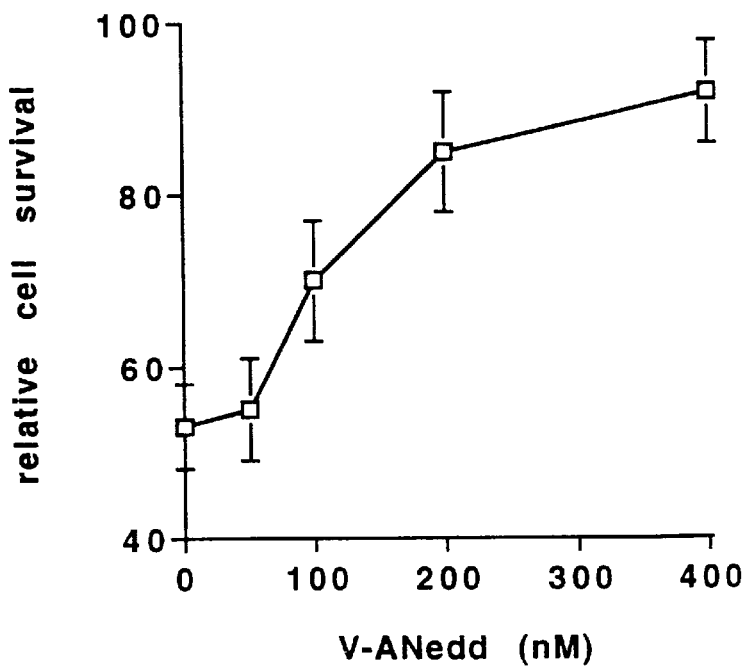
Figure 4C:
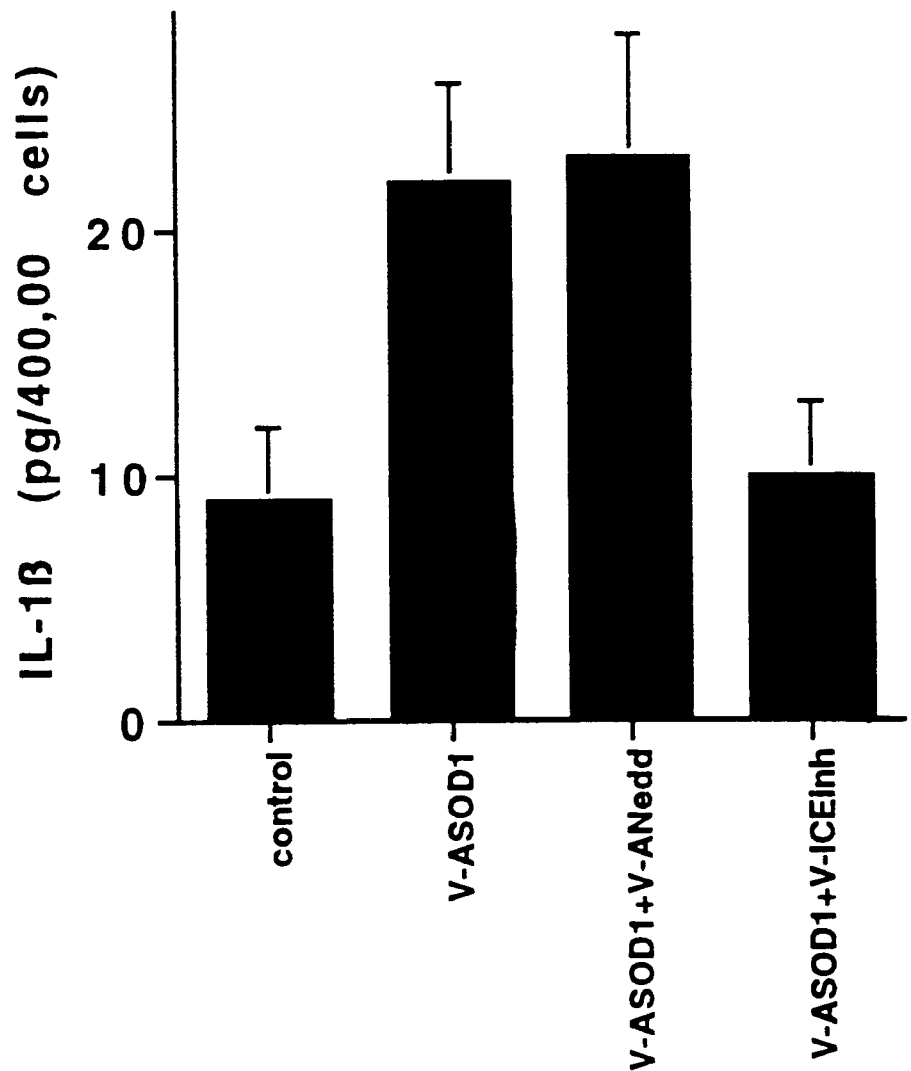

FIGS. 4A, 4B and 4C. V-ANedd rescues PC12 cells from serum deprivation but not from SOD1 down-regulation. (FIG. 4A) V-ANedd differentially protects PC12 cells from serum deprivation. For serum deprivation (4 left-hand bars) cells were extensively washed as described in Experimental Procedures hereinbelow and the indicated additives (100 ng/ml NGF, 400 nM V-ANedd, or 200 nM V-ICEinh were added at the time of plating in serum-free RPMI1640 medium. For SOD1 down-regulation (4 right-hand bars), PC12 cells were re-plated on fresh collagen-coated 24-well dishes in complete medium (RPMI 1640 medium with 10% horse serum, 5% fetal bovine serum) with 50 nM V-ASOD1 (vector linked antisense oligonucleotide to SOD1). Additives (800 nM V-ANedd, 25 nM V-ICE$_{inh}$) were included as indicated. Control cells were in complete medium. Cultures were incubated for 24 hours, lysed and number of intact nuclei counted. The numbers of surviving cells are expressed relative to the number in the control cultures (designated as 100). Here, as in past studies (Greene and Tischler, 1976; Rukenstein et al., 1991; Troy et al., 1996a,b), NGF or complete medium promotes survival of all cells initially plated. Experiments were performed in triplicate wells and data are expressed as means ±SEM. (FIG. 4B)

Dose-response curve for protection from serum deprivation by V-ANedd. PC12 cells were washed for trophic factor deprivation and plated in serum-free medium with the indicated concentrations of V-ANedd. Cell survival relative to the number present with the addition of NGF was measured at one day.

(FIG. 4C) V-ANedd does not block the V-ASOD1-induced increase of IL-1β production. PC12 cells were plated with the indicated additives (50 nM V-ASOD1, 25 nM V-ICE$_{inh}$, 800 nM V-ANedd). Controls contained complete medium. After 20 hours, media were removed and IL-1β was measured by ELISA using the Intertest-1βX® kit. Data are expressed as means ±SEM (n=3).

Figure 5A:
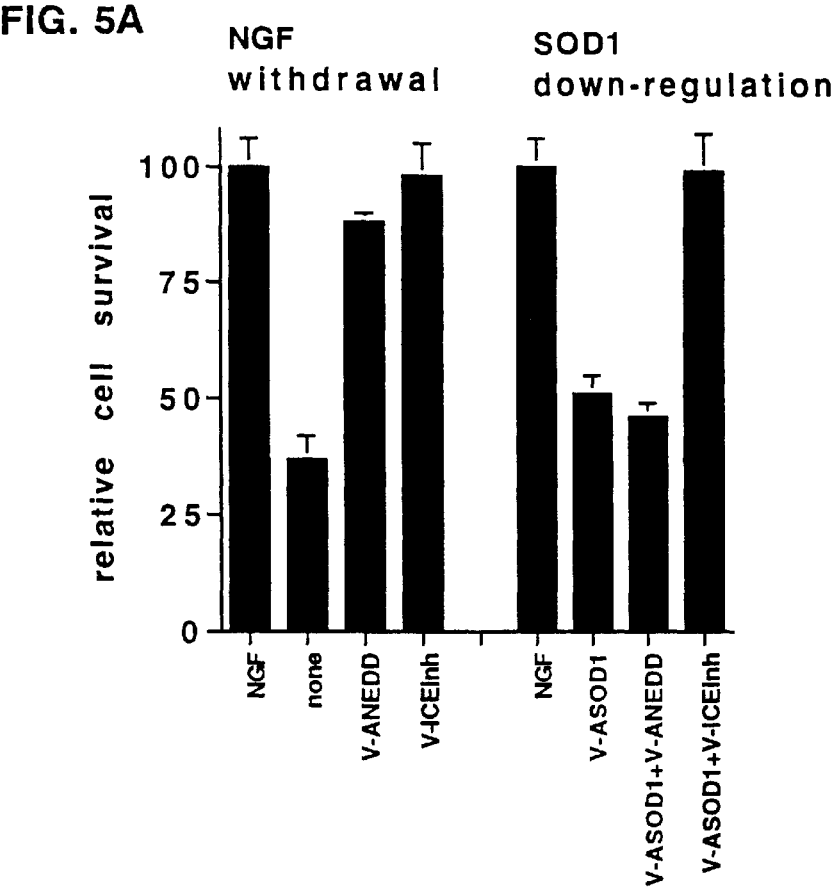
Figure 5B:
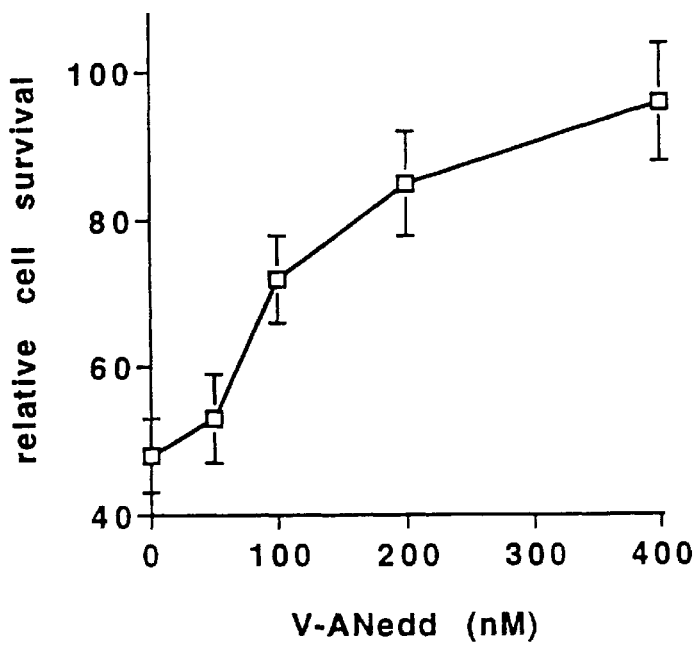
Figure 5C:
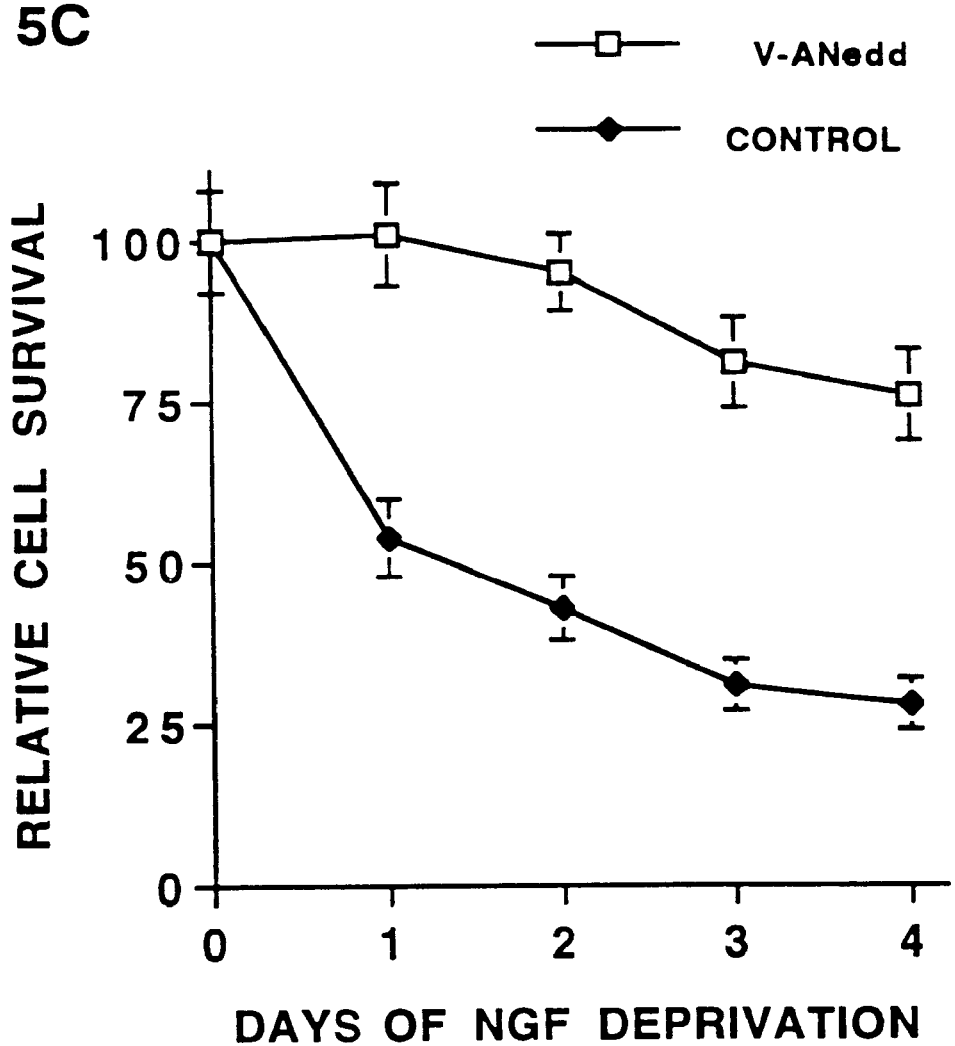

FIGS. 5A, 5B and 5C. Neuronally differentiated PC12 cells are rescued from NGF deprivation, but not from SOD1 down-regulation by V-ANedd.

(FIG. 5A) V-ANedd differentially protects neuronally differentiated PC12 cells from apoptosis caused by NGF withdrawal. PC12 cells were neuronally differentiated by exposure to NGF (100 ng/ml) for at least 7 days in RPMI 1640 medium plus 1% horse serum. Cells were deprived of serum and NGF and re-plated as described in FIGS. 4A–C. Additives present at the time of plating included 400 nM V-ANedd, 400 nM V-ICE$_{inh}$, or 100 ng/ml NGF (4 left-hand bars). For SOD1 down-regulation (4 right-hand bars) neuronally differentiated PC12 cells were plated in RPMI 1640 medium plus 1% horse serum, with 100 ng/ml NGF. At the time of plating, cultures were incubated, as indicated, with 50 nM V-ASOD1 and with the indicated additives (800 nM V-ANedd, 50 nM V-ICE$_{inh}$). Cell survival was determined after one day and expressed as in FIGS. 4A–C.

(FIG. 5B) Dose-response curve for protection from NGF deprivation by V-ANedd. Neuronally differentiated PC12 cells were washed as above for NGF deprivation and plated in serum-free medium with the indicated concentrations of V-ANedd. Cell survival relative to the number present with the addition of NGF was quantified at one day.

(FIG. 5C) V-ANedd provides long term protection against NGF deprivation. Neuronally differentiated PC12 cells were deprived of NGF and serum and plated as described in FIG. 5A. V-ANedd (400 nM) was included at the time of NGF deprivation and replenished 1 day later. Cell survival was determined at the indicated times as in FIGS. 4A–C.

Figure 6A:
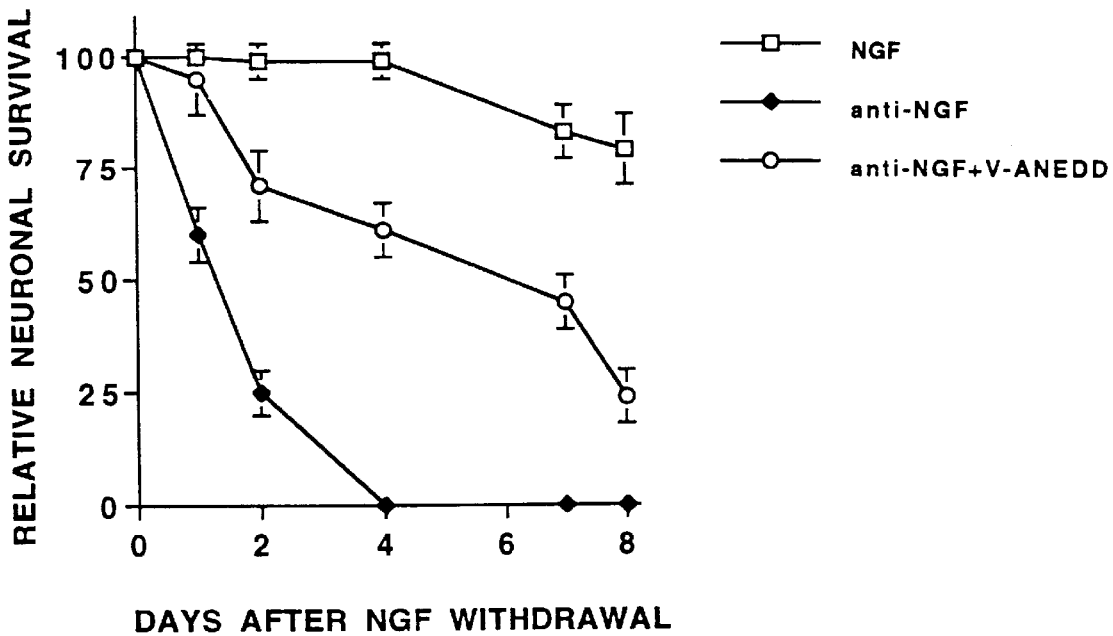
Figure 6B:
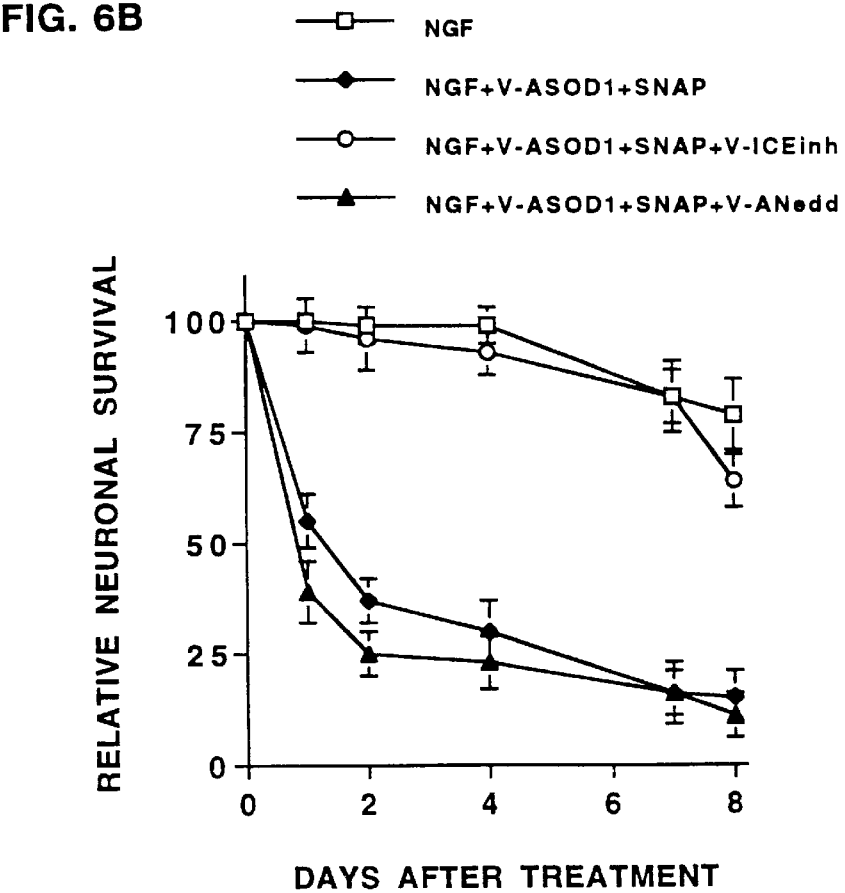

FIGS. 6A–6B. V-ANedd protects sympathetic neurons from NGF withdrawal, but not from oxidative stress.

(FIG. 6A) V-ANedd protects sympathetic neurons from NGF-withdrawal. At the time of NGF deprivation, V-ANedd (400 nM) was added to the cultures as indicated. Numbers of surviving neurons were determined at the indicated times as described in Experimental Procedures hereinbelow and are reported as relative to the number present in each culture at the time of NGF withdrawal.

(FIG. 6B) V-ANedd does not protect sympathetic neurons from death induced by SOD1 down-regulation and nitric oxide generation. Sympathetic neurons, after 6 days in culture, were maintained with NGF (100 ng/ml) and mixtures of the following additives as indicated: V-ASOD1 (50 nM), SNAP (100 μM) and V-ANedd (400 nM). Numbers of surviving neurons were determined at the indicated times as above.

FIGS. 7A–7I. Morphology of cells rescued by V-ANedd.

Photomicrographs of cells treated as described in the preceding figures. FIGS. 7A–C, naive PC12 cells: FIG. 7A, in serum-free RPMI 1640 medium with 100 ng/ml NGF (24 hr); FIG. 7B, in RPMI 1640 medium alone (24 hr); FIG. 7C, in serum-free RPMI 1640 medium with 400 nM V-ANedd (24 hr). FIGS. 7D–F, neuronally differentiated PC12 cells FIG. 7D, re-plated in serum-free RPMI 1640 medium with 100 ng/ml NGF (24 hr); FIG. 7E, re-plated in serum-free RPMI 1640 medium without NGF (24 hr); FIG. 7F, re-plated in serum-free RPMI 1640 medium with 400 nM V-ANedd (24 hr). FIGS. 7G–I, sympathetic neurons: FIG. 7G, cultured with 100 ng/ml NGF (3 days); FIG. 7H, cultured in NGF-free medium with anti-NGF (3 days); FIG. 7I, cultured in NGF-free medium with anti-NGF plus 400 nM V-ANedd (3 days). Phase contrast optics. x180.

DETAILED DESCRIPTION OF THE INVENTION

The present invention provides for an oligonucleotide having the sequence 5'GCTCGGCGCCGCCATTTCCAG3' (SEQ ID No. 1). The present invention also provides for an oligonucleotide having the sequence 5'GTCAGCGGCCAT-CAGCTT3' (SEQ. ID No. 2). The present invention also provides for variants of these oligonucleotide sequences which conserve their biological activity. It is known to one of skill in the art that certain variations of nucleotides in an oligonucleotide will not affect the biological activity. The present invention provides for an oligonucleotide which is capable of inhibiting the expression of a Nedd2 rodent gene or inhibiting the expression of a human Ich-1L gene by antisense inhibition of translation. The full sequence of Ich-1L has been deposited in GenBank at accession number (code) U13021. The oligonucleotide may comprise DNA, cDNA or synthetic oligonucleotides.

The present invention also provides for a compound comprising the oligonucleotide having the sequence 5'GCTCGGCGCCGCCATTTCCAG3' (SEQ ID No. 1) and an agent capable of specifically directing the compound to a cell. The present invention also provides for a compound comprising the oligonucleotide having the sequence 5'GTCAGCGGCCATCAGCTT3' (SEQ. ID No. 2) and an agent capable of specifically directing the compound to a cell. The compound may comprise any variants of the sequence 5'GCTCGGCGCCGCCATTTCCAG3' (SEQ ID No. 1) or of the sequence 5'GTCAGCGGCCATCAGCTT3' (SEQ. ID No. 2) which do not change their respective biological activity. The agent may comprise a polypeptide comprising at least a portion of an Antennapedia polypeptide. In one embodiment of the present invention, the agent comprises at least a portion of a polypeptide comprising the sequence NPyS-Arg-Gln-Ile-Lys-Ile-Trp-Phe-Gln-Asn-Arg-Arg-Met-Lys-Trp-Lys-Lys-(Seq. I.D. No. 3).

As used herein, biological activity of 5'GCTCGGCGC-CGCCATTTCCAG3' (SEQ ID No. 1) comprises any antisense activity particular to this oligonucleotide, inhibition of the rodent Nedd2 gene, binding to and inhibiting translation of Nedd2 mRNA, binding to and inhibiting transcription of Nedd2 DNA or cDNA, inhibiting the expression of any protein of the interleukin-1 converting enzyme family member, inhibiting cell death, inhibiting apoptosis.

As used herein, biological activity of 5'GTCAGCGGC-CATCAGCTT3' (SEQ. ID No. 2) comprises any antisense activity particular to this oligonucleotide, inhibition of the human Ich-1L gene, binding to and inhibiting translation of Ich-1L mRNA, binding to and inhibiting transcription of Ich-1L DNA or cDNA, inhibiting the expression of any protein of the interleukin-1 converting enzyme family member, inhibiting cell death, inhibiting apoptosis.

In another embodiment of the present invention, the compound may comprise NPyS-Arg-Gln-Ile-Lys-Ile-Trp-Phe-Gln-Asn-Arg-ArgMet-Lys-Trp-Lys-GCTCGGCGCCGCCATTTCCAG (SEQ ID Nos. 4 and 5).

The agent may comprise an antibody, an adjuvant or a cell-specific ligand. The agent may further comprise Penetratin1®.

In the practice of the present invention, the cell may be a neuronal cell.

The present invention also provides for a pharmaceutical composition comprising an oligonucleotide having the sequence 5'GCTCGGCGCCGCCATTTCCAG3' (SEQ ID No. 1) or variants thereof and a pharmaceutically acceptable carrier. The present invention provides for a pharmaceutical composition comprising an oligonucleotide having the sequence 5'GTCAGCGGCCATCAGCTT3' (SEQ. ID No. 2) or variants thereof and a pharmaceutically acceptable carrier.

The carrier may comprise a diluent, an appropriate adjuvant, a herpes virus, a liposome, a microencapsule, a neuronal cell receptor ligand, a neuronal-specific virus, a polymer encapsulated cell or a retroviral vector.

The pharmaceutically acceptable carrier may be in the form of an aerosol, intravenous, oral or topical carrier.

The present invention also provides for a method of inhibiting trophic factor withdrawal mediated death of a cell which comprises contacting the cell with an amount of the oligonucleotide having the sequence 5'GCTCGGCGCCGC-CATTTCCAG3' (SEQ ID No. 1) effective to inhibit death of the cell.

The cell may be found in a subject. The subject may be a human. The cell may be a brain cell, a spinal cord cell, neuronal cell.

The agent may comprise a polypeptide encompassing at least a portion of an Antennepedia polypeptide. The agent may include a polypeptide having the sequence NPyS-Arg-Gln-Ile-Lys-IleTrp-Phe-Gln-Asn-Arg-Arg-Met-Lys-Trp-Lys-Lys-(Seq. I.D. No. 3). The agent may comprise an antibody, an adjuvant or a cell-specific ligand.

The present invention also provides for a method for treating a neurodegenerative disorder in a subject which comprises administering to the subject a compound which comprises an oligonucleotide having the sequence 5'GCTCGGCGCCGCCATTTCCAG3' (SEQ ID No. 1) or 5'GTCAGCGGCCATCAGCTT3' (SEQ. ID No. 2) or any variants thereof, and an agent capable of directing delivery of the compound to a cell, the compound being present in an amount effective to inhibit neuronal cell death and thus treat the neurodegenerative disorder in the subject.

In the practice of this invention the neurodegenerative disorder may associated with aging, amyotrophic lateral sclerosis, Alzheimer's disease, dentatorubral and pallidoly-usian atrophy, Huntington's disease, Machoado-Joseph disease, multiple sclerosis, muscular dystrophy, Parkinson's disease, senility, spinocerebellar ataxia type I, spinobulbar muscular atrophy, stroke, trauma.

The administration may comprise aerosol delivery; intralesional, intraperitoneal, intramuscular or intravenous injection; infusion; liposome-mediated delivery; anal, nasal, oral, ocular, otic or topical delivery of the pharmaceutical composition.

One of skill in the art would know methods of introducing a compound or oligonucleotide of the present invention into a cell or into a subject. Methods of incorporation of nucleic acid molecules into liposomes are well known to those of ordinary skill in the art. In another embodiment of this method, the oligonucleotide may be delivered via transfection, injection, or viral infection. There are several protocols for human gene therapy which have been approved for use by the Recombinant DNA Advisory Committee (RAC) which conform to a general protocol of target cell infection and administration of transfected cells (see for example, Blaese, R. M., et al., 1990; Anderson, W. F., 1992; Culver, K. W. et al., 1991). In addition, U.S. Pat. No. 5,399,346 (Anderson, W. F. et al., issued Mar. 21, 1995) describes procedures for retroviral gene transfer. The contents of these support references are incorporated in their entirety into the subject application. Retroviral-mediated gene transfer requires target cells which are undergoing cell division in order to achieve stable integration hence, cells are collected from a subject often by removing blood or bone marrow.

Several methods have been developed over the last decade for the transduction of genes into mammalian cells for potential use in gene therapy. In addition to direct use of plasmid DNA to transfer genes, episomal vectors, retroviruses, adenoviruses, parvoviruses, and herpesviruses have been used (Anderson et al., 1995; Mulligan, 1993; The contents of which are incorporated in their entirety into the subject application). For transfer of genes into cells ex vivo and subsequent reintroduction into a host, as would be most feasible in immunodeficiency patients, retroviruses have been the vectors of choice.

Throughout this application, the following standard abbreviations are used throughout the specification to indicate specific nucleotides:

| C = cytosine | A = adenosine |
| T = thymidine | G = guanosine |

The DNA molecules and the oligonucleotides of the subject invention also include DNA molecules coding for polypeptide analogs, fragments or derivatives of oligonucleotides which differ from naturally-occurring forms in terms of the identity or location of one or more nucleotide bases (deletion analogs containing less than all of the bases specified for the molecule, substitution analogs wherein one or more bases specified are replaced by other bases and addition analogs wherein one or more nucleotide bases is added to a terminal or medial portion of the oligonucleotide) and which share some or all properties of naturally-occurring forms. These include: the incorporation of bases "preferred" for mammalian hosts; the provision of sites for cleavage by restriction endonuclease enzymes; and the provision of additional initial, terminal or intermediate DNA sequences that facilitate construction of readily expressed vectors.

The compound of the present invention may have increased stability, efficacy, potency and bioavailability by virtue of the agent or by virtue of the oligonucleotide. Further, the compound may have decreased toxicity. The compound may have enhanced mucosal intestinal permeability. The compound may be synthetically prepared. The compound of the present invention may include L-,D- or unnatural amino acids, alpha, alpha-disubstituted amino acids, N-alkyl amino acids, lactic acid (an isoelectronic analog of alanine). The peptide backbone of the compound may have at least one bond replaced with PSI[CH=CH] (Kempf et al. 1991). The compound may further include trifluorotyrosine, p-Cl-phenylalanine, p-Br-phenylalanine, poly-L-propargylglycine, poly-D,L-allyl glycine, or poly-L-allyl glycine.

One embodiment of the present invention is a peptidomimetic compound having the biological activity of the structure NPyS-Arg-Gln-Ile-Lys-Ile-Trp-Phe-Gln-Asn-Arg-Arg-Met-Lys-Trp-Lys GCTCGGCGCCGCCATTTCCAG (SEQ ID Nos. 4 and 5) or NPyS-Arg-Gln-Ile-LysIle-Trp-Phe-Gln-Asn-Arg-Arg-Met-Lys-Trp-Lys-Lys GTCAGCG-GCCATCAGCTT (SEQ. ID Nos. 6 and 7) wherein the compound has a bond, a peptide backbone or an amino acid component replaced with a suitable mimic. Examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, cysteine (acetamindomethyl), N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, Boc-L-thioproline. (Blondelle, et al. 1994; Pinilla, et al. 1995).

Another embodiment of the present invention is a method for alleviating symptoms of a neurodegenerative disorder in a subject which includes administering to the subject the compounds described hereinabove, the compound being present in an amount effective to inhibit neuronal cell death and thus alleviate the symptoms of the neurodegenerative disorder in the subject.

The neurodegenerative disorder may be associated with aging, Alzheimer's disease, amyotrophic lateral sclerosis, multiple sclerosis, muscular dystrophy, Parkinson's disease, senility, spinocerebellar ataxia type I, spinobulbar muscular atrophy, stroke, trauma. The subject may be a mammal. The mammal may be a human. The administration may include aerosol delivery; intralesional, intraperitoneal, intramuscular or intravenous injection; infusion; liposome-mediated delivery; anal, nasal, oral, ocular, otic or topical delivery of the pharmaceutical composition.

The effectiveness of the compounds described herein to prevent trophic factor withdrawal mediated cell death is a surprising result that would not have been anticipated by one skilled in the art. The specific sequences used in the anti-sense oligonucleotides as described herein provide unexpected results in the prevention and inhibition of cell death mediated by trophic factor withdrawal.

As used herein "trophic factor" encompasses the family of neurotrophins. Some examples of neurotrophic factors are NGF, BDNF, NT3, NT4, GDNF. Other neurotrophic factors and trophic factors would be known to one of ordinary skill in the art.

Also provided by the invention are pharmaceutical compositions comprising therapeutically effective amounts of polypeptide products of the invention together with suitable diluents, preservatives, solubilizers, emulsifiers, adjuvants and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. The choice of compositions will depend on the physical and chemical properties of the protein having the activity of inhibiting neuronal cell death. For example, a product derived from a membrane-bound form of the protein may require a formulation containing detergent. Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal, oral, injection or infusion by intravenous, intraperitoneal, intracerebral, intramuscular, intraocular, intraarterial or intralesional.

The present invention includes a delivery system which links the polypeptide to an agent which directs the polypeptide to neuronal cells in order to facilitate entry into the cells. The Antennepedia protein may be used as such a delivery agent. The invention also includes therapeutic uses of the isolated polypeptide to prevent trophic factor withdrawal mediated cell death. Related therapeutic uses include treating stroke, trauma, neurodegenerative disorders or regenerating neurons, cardiac ischemia, liver disease, pulmonary disease, congestive heart disease, myocardial infarction, ALS, Alzheimer's disease, Parkinson's disease, senility, aging, muscular dystrophy, multiple sclerosis, Huntington's disease, spinocerebellar ataxia type I, Machoado-Joseph disease, spinobulbar muscular atrophy or dentatorubral and pallidolyusian atrophy.

This invention is illustrated in the Experimental Detail section which follows. These sections are set forth to aid in an understanding of the invention but are not intended to, and should not be construed to, limit in any way the invention as set forth in the claims which follow thereafter.

EXPERIMENTAL DETAILS
EXAMPLE 1:Nedd2 IS REQUIRED FOR APOPTOSIS FOLLOWING TROPHIC FACTOR WITHDRAWAL BUT NOT SOD1 DOWN-REGULATION IN SYMPATHETIC NEURONS AND PC12 CELLS Abstract: Differential requirements for Nedd2 in apoptosis Activation of cysteine aspartases (caspases) appears to be a required element of apoptotic death in many paradigms. It has been shown that general inhibitors of cysteine aspartases block apoptosis of PC12 cells and sympathetic neurons evoked by either trophic factor (NGF and/or serum) deprivation or SOD1 down-regulation. Moreover, activation of a caspase family member similar or equivalent to the interleukin-1β converting enzyme (ICE) was implicated for death due to SOD1 down-regulation, but not withdrawal of trophic support. The experiments presented here demonstrate that diminished expression of the cysteine aspartase Nedd2 in PC12 cells and sympathetic neurons induced by an appropriate vector-peptide-linked antisense oligonucleotide rescues them from death due to trophic factor deprivation without inhibiting apoptosis in the same cell types evoked by SOD1 down-regulation. Neither the level (as revealed by western immunoblotting) nor the cellular distribution (as revealed immunohistochemically) of Nedd2 were demonstrably altered by trophic factor deprivation. However, evidence for proteolytic processing of Nedd2 (consistent with commencement of activation) was observed in PC12 cells after withdrawal of trophic support. These findings indicate that neuronal death triggered by different initial causes may be mediated by distinct members of the cysteine aspartase family.

In particular, inhibition studies implicate cysteine aspartases as obligate elements of the cell death mechanism in both initiating causes of death (Troy et al., 1996b). However, even at the level of cysteine aspartases, findings have suggested the presence of parallel pathways. Apoptosis following SOD1 down-regulation is suppressed by the peptide YVAD, a potent inhibitor of the interleukin-1 converting enzyme (ICE), by blocking antibodies to IL-1β and by the IL-1 receptor antagonist IL-1Ra, while such agents have little or no effect on death caused by trophic factor/NGF withdrawal. These findings suggest that ICE itself, or another enzyme with pro-IL-1β cleaving activity is required for death in the SOD1 down-regulation paradigm whereas a different cysteine aspartame is required for death in the case of trophic factor deprivation (Troy et al., 1996b).

In light of the above, one object of the present study was to identify a specific cysteine aspartase that is required for neuronal apoptosis triggered by trophic factor deprivation. The cysteine aspartase Nedd2 is the rodent homologue of the human Ich-1/NEDD2 ICE-family member and is highly expressed in neurons and PC12 cells (Kumar et al., 1994). Over-expression of Nedd2/Ich-1 causes apoptosis in fibroblasts and neuroblastoma cells (Kumar et al., 1994) and expression of a NEDD2 antisense construct protects a hematopoietic-derived cell line from death evoked by cytokine deprivation (Kumar, 1995). In the experiments reported here, a designed vector-linked antisense oligonucleotide was used to suppress Nedd2 expression in cultured PC12 cells and sympathetic neurons. The findings herein indicate that Nedd2 plays a required role in neuronal apoptosis caused by loss of trophic support. In contrast, it does not appear to be required for death caused by SOD1 downregulation and thus, distinct cysteine aspartases mediate neuronal apoptosis triggered by different causes in the same cell.

Materials and Methods—Cell Culture, PC12 cells

PC12 cells were grown as previously described (Greene and Tischler, 1976) on rat-tail collagen-coated dishes in RPMI 1640 medium containing 5k fetal calf serum and 10k heat-inactivated horse serum (complete medium). NGF primed (neuronally differentiated) PC12 cells were grown for at least 7 days in RPMI 1640 medium plus 1% horse serum and NGF (100 ng/ml). For cell survival assays involving trophic factor deprivation, cells (either naive or NGF-pretreated) were extensively washed in serum-free RPMI 1640 medium and re-plated on fresh collagen-coated 24-well dishes as previously described (Rukenstein et al., 1991) in RPMI 1640 medium lacking serum or NGF. For SOD1 down-regulation survival assays, cells were re-plated in complete medium with V-ASOD1 (vector linked antisense oligonucleotide to SOD1, 50 nM), as previously described (Troy et al., 1996a). Various concentrations of V-ANedd (vector linked antisense oligonucleotide to Nedd2) were included in the medium as indicated. Numbers of viable cells per culture were determined by quantifying intact nuclei as previously described (Rukenstein et al., 1991). Counts were performed in triplicate and reported as means ±SEM.

Sympathetic neurons

Sympathetic neuron cultures were prepared from 2 day old rat pups, as previously described (Ferrari et al., 1995). Cultures were grown in 24-well collagen coated dishes in RPMI 1640 medium plus 10% horse serum with mouse NGF (100 ng/ml). One day following plating, uridine and 5-fluorodeoxyuridine (10 µM each) were added to the cultures and left for three days to eliminate non-neuronal cells. On the sixth day following plating NGF was removed by washing the cultures three times with RPMI 1640 medium plus 10% horse serum, followed by the addition of medium containing anti-mouse NGF (1:200, Sigma, St. Louis, Mo.) with or without V-ANedd. Each culture was scored, as previously described (Rydel and Greene, 1988), as numbers of living, phase-bright neurons at various times. Three replicate cultures were assessed for each condition and data are normalized to numbers of neurons present in each culture at the time of NGF withdrawal and reported as mean ±SEM.

Synthesis of V-ANedd

Oligonucleotides bearing an SH group at their 5' end and an NH group at their 3' end were purchased from Operon® (Alameda, Calif.). As previously described (Troy et al., 1996a) oligonucleotides were resuspended in deionized water, an equimolar ratio of Penetratin 1® (Oncor, Gaithersburg, Md.) was added and the mixture was incubated at 37;C. for 1 hour. The yield of the reaction, estimated by SDS-PAGE followed by Coomassie blue staining, was routinely above 50%. A scrambled sequence of the antisense oligonucleotide (same base composition, different order), defined as V-SNedd, was synthesized for use as a control,.

Antibody preparation

Anti-N-Nedd2, a polyclonal rabbit antiserum was produced for us by Multiple Peptide Systems (San Diego, Calif.) using a 16 amino acid synthetic peptide homologous to the N-terminus (amino acids 1–16) as the antigen. The antiserum was affinity purified with peptide bound to Sulfo-Link® gel. Antiserum against a C-terminal peptide of Nedd2 (Nedd2 p12 C20) was purchased from Santa Cruz Biotechnology (Santa Cruz, Calif.).

Immunofluorescence

PC12 cells were plated on coverslips or on 8 well multichamber slides (LabTek, VWR), coated with Matrigel®. After growth overnight, cells were fixed in ice cold methanol and then immunostained as described (Troy et al., 1990). The primary antibody was either affinity purified antibody Anti-N-Nedd2 or Nedd2 p12 C20 (Santa Cruz Biotechnology) at a dilution of 1:200. The secondary antibody was fluoroscein isothiocyanate-conjugated goat anti-rabbit (Cappel, Durham, NC) at 1:100. For visualization with a Nikon® fluorescence microscope slides were coverslipped with Aqua-mount®. Confocal microscopy was done on a BioRad® 600 confocal microscope.

Western blotting

PC12 cells grown with or without V-ANedd or V-SNedd were harvested in SDS-containing sample buffer and immediately boiled. Equal amounts of protein were separated by 10% PAGE, transferred to nitrocellulose and immunostained as described (Troy et al., 1992). The affinity purified anti-N-Nedd2 was used at a dilution of 1:500. The commercial antiserum, Nedd2 p12 C20 (Santa Cruz Biotechnology), was used at a dilution of 1:350. Visualization was with ECL using goat-anti-rabbit peroxidase at 1:1000. The relative intensity of the protein bands were quantified using Scion Image 1.55® software and samples were normalized by stripping and reprobing the blots with anti-peripherin antibody.

Assay of IL-1β

IL-1β was quantified by ELISA using the Intertest-1βX® kit (Genzyme, Cambridge, Mass.) as previously described (Troy et al., 1996b). PC12 cells were grown as described above, on 24-well plates, in 500 µl of medium. After one day incubation, medium was removed and IL-1β measured following the manufacturer's instructions, and number of viable cells in each well quantified.

Results

A vector-linked Nedd2 antisense oligonucleotide (V-ANedd) down-regulates Nedd2 protein To suppress expression of Nedd2 in neuronal cells, an antisense oligonucleotide was designed corresponding to the last 12 bases in the 5' UTR and the first 9 bases in the coding region of the Nedd2 transcript (Kumar et al., 1994). The antisense oligonucleotide (ANedd; GCTCGGCGCCGCCATTTCCAG) (SEQ ID No. 1) is not homologous to any other reported mRNA sequence, including those of the other known cysteine aspartases. The oligonucleotide was linked to the vector peptide Penetratin 1® (V-) (Theodore et al., 1995; Troy et al., 1996a) to enhance its uptake by cells. The control scrambled oligonucleotide (SNedd; CCGTAGCGTAGCTCCGCCTGC) (SEQ ID No. 2) was also linked to vector peptide. This vector linked strategy significantly enhances the potency of antisense oligonucleotides and permits their use in the presence of serum (Troy et al., 1996a).

Using an affinity purified anti-peptide antiserum (anti-N-Nedd2) generated against a synthetic N-terminal Nedd2 peptide, the expression of Nedd2 was examined in naive and neuronal PC12 cells before and after exposure to V-ANedd. As revealed by immunohistochemistry, in control cells the anti-N-Nedd2 staining was primarily cytoplasmic. This decreased to almost undetectable levels when the cells were pretreated for 24 hours with 400 nM V-ANedd (FIGS. 1A–1D). In contrast, no change in staining was observed after exposure to 400 nM V-SNedd. Comparable results were found with another antibody generated to a C-terminal peptide of Nedd2. Confocal microscopy with either the N-terminal (FIGS. 2A–D) or the C-terminal antiserum demonstrated that the Nedd2 staining pattern does not change substantially after 20 hrs. of trophic factor deprivation (FIGS. 2A–D) in either naive or neuronal PC12 cells, or after SOD1 down-regulation. In all cases staining was largely cytoplasmic with 1–2 foci of staining seen in many nuclei. In the case of anti-N-Nedd2, all staining was abolished by preincubation with the immunizing peptide. By Western blot analysis anti-N-Nedd2 recognizes a major band at 53 kD in whole PC12 cell lysates (FIG. 3A). The same major band was identified with the C-Nedd antibody (FIG. 3B). This apparent molecular weight is in agreement with that calculated from the predicted sequence of the Nedd2 protein (51 kD). There are also 3 bands of lesser intensity seen with both antibodies at 70 kD, 60 kD and 45 kD. An identical pattern was seen with neuronally differentiated PC12 cells and a similar pattern with cultured sympathetic neurons. Specificity was assessed by absorption of the antiserum with the peptide to which it was generated and showed loss of signal by each of the above species. A minor band at 19 kD was seen on occasion at varying intensity when the N-terminal antibody was used. The major band and the additional molecular weight minor bands are down-regulated by 60–70% (n=4) after 18–22 hours treatment with V-ANedd (FIGS. 3A–B). In contrast, there was no down-regulation of CPP-32 on blots of the same samples probed with anti-CPP32, indicating specificity of V-ANedd treatment for Nedd2. V-SNedd, the control oligonucleotide, did not down-regulate any of the bands. None of the bands detected by Western blot appeared to be up or down regulated to a substantial degree in response to either trophic factor withdrawal or short (2–24 hrs) or long-term (10–14 days) NGF treatment. However, after withdrawal of trophic support from naive or primed PC12 cells a cleavage product of approximately 36 kD was detectable by immunoblotting with the N-terminal antiserum prior to onset of cell death.

Differential effects of V-ANedd on PC12 cell death

To evoke apoptotic neuronal death by trophic factor deprivation, nerve growth factor (NGF) and/or serum was withdrawn from cultures of PC12 cells (either naive, or neuronally differentiated by NGF-pretreatment (Greene and Tischler, 1976) and neonatal rat sympathetic neurons (Rydel and Greene, 1988; Ferrari et al., 1995; Troy et al., 1996a). Oxidative stress was induced by exposing cultures to the V-linked copper/zinc superoxide dismutase (SOD1) antisense construct V-ASOD1 which down-regulates SOD1 and induces apoptosis in PC12 cells (Troy and Shelanski, 1994; Troy et al, 1996a–c). In each of these paradigms, approximately 40–60 % of the cells undergo apoptosis within 24 hrs.

V-ANedd protects naive PC12 cells from death caused by serum deprivation, with maximal protection at 400 nM when added at the same time as serum withdrawal (FIGS. 4A–C, 7A–I). In this and all subsequent experiments, the scrambled V-SNedd construct had no effect on survival or death. Pretreatment of cultures for 4 hours with 50 nM V-ANedd shifted the dose-response curve to the left so that maximal survival was obtained with 100 nM V-ANedd. In contrast, there was no protection from SOD1 down-regulation, even at 800 nM (FIGS. 4A–C), and pretreatment with V-ANedd was without effect. However, V-ANedd did down-regulate Nedd2 in the presence of V-ASOD1, precluding competition by the two vector-linked constructs for cell entry. The same concentrations of V-ANedd also protected neuronally differentiated PC12 cells from apoptosis caused by NGF withdrawal (FIG. 5A), but again, not from down-regulation of SOD1 (FIG. 5B). Two successive additions of V-ANedd, at the time of NGF deprivation and one day later, maintained survival of greater than 754 of the cells through 4 days (FIG. 5C). Although V-ANedd maintained survival, it did not mimic the actions of NGF in promoting either rapid flattening of naive PC12 cells or neurite outgrowth from neuronally-differentiated cells (FIGS. 7A–I).

Death of PC12 cells evoked by SOD1 down-regulation, but not by withdrawal of trophic support, is associated with enhanced release of IL-1§ and this is blocked by the general inhibitor of cysteine aspartase activity V-IQACRG (V-ICE$_{inh}$)(Troy et al., 1996b). As illustrated in FIG. 4C, V-ANedd did not affect IL-1β release after exposure to ASOD1. This indicates that V-ANedd does not affect processing of pro-IL-1β and that this is not the mechanism by which it blocks death due to trophic factor deprivation. The data in FIGS. 4A–C and 5A–C also show that, as expected, V-ICE$_{inh}$ protects cells from both trophic factor deprivation and SOD1 downregulation.

V-ANedd protects sympathetic neurons from NGF deprivation, but not from oxidative stress.

Parallel results were obtained with sympathetic neurons subjected to NGF deprivation. A single addition of V-ANedd at the time of NGF withdrawal resulted in over 60% survival after 4 days and 25% survival at 8 days; at these times, all neurons in control cultures were dead (FIGS. 6A–B). Although V-ANedd promoted survival, it did not maintain the neurites of NGF-deprived neurons (FIGS. 7A–I). Readdition of NGF to such cultures resulted in the reappearance of healthy neurites and maintenance of cell number, thereby confirming neuronal survival and function in the presence of V-ANedd.

Exposure of cultured sympathetic neurons to antisense SOD1 alone has proved insufficient to produce death, even though, as for PC12 cells, this treatment reduces SOD1 levels by 50%. In PC12 cell cultures, death due to SOD1 down-regulation requires endogenous NO (nitric oxide) synthase activity and appears due to generation of peroxynitrite (Troy et al., 1996a). Consistent with this, when V-ASOD1 and the NO generator, SNAP (S-nitrosopenicillamine) were added simultaneously to cultured sympathetic neurons, even in the presence of NGF, approximately 50% of the cells underwent apoptotic death within 24 hours. Treatment with the NO generator in the absence of SOD1 downregulation did not produce death of either sympathetic neurons or PC12 cells (Farinelli et al., 1996). As in the study with PC12 cells (Troy et al., 1996b), the general inhibitor of cysteine aspartase activity, V-IQACRG (V-ICE$_{inh}$), prevented sympathetic neuron death evoked by V-ASOD1+SNAP (FIGS. 6A–B). In contrast, V-ANedd was without effect in this paradigm (FIG. 6B).

Discussion

In the present studies, an antisense construct was designed and used to down-regulate the cysteine aspartase Nedd2 in neuronal cells and it was found that this inhibited death caused by withdrawal of trophic support, but not by oxidative stress. Multiple aspects of the studies support the specificity and utility of these reagents. The major species recognized by both our N-terminal Nedd2 antiserum and a Nedd2 C-terminal antiserum on Western blots migrated at an apparent Mr of 53 kD. This corresponds closely to the predicted Mr of the Nedd2 protein based on the sequence of the nedd2 transcript from mouse (Kumar 1995) as well as rat. Recognition of this species by anti-N-Nedd2 was abolished in the presence of excess immunizing peptide. Both antisera also provided similar patterns of cellular staining which, in the case of anti-N-Nedd2, was eliminated by preincubation with the immunizing peptide. Exposure to the V-ANedd antisense construct yielded significant down-regulation of Nedd2 protein as assessed by Western blotting and immunostaining with the two different antisera. To assess the specificity of the antisense construct, V-SNedd, a scrambled version of V-ANedd was also tested and it was observed that it did not affect either Nedd2 protein levels, staining of cells with anti-Nedd2 or cell death. Moreover, the observation that V-ANedd does not promote survival of neuronal cells after SOD1down-regulation appears to rule out non-specific anti-apoptotic actions of this construct. Finally, V-ANedd effectively suppressed death of serum-deprived naive PC12 cells. In such cultures, apoptosis does not require de novo protein translation (Rukenstein et al, 1991), and thus this finding appears to exclude potential non-specific effects of the antisense construct on synthesis of proteins required for death.

The results of these experiments argue for the existence of at least two distinct parallel pathways to apoptotic cell death in the same neuron. The choice of one or the other pathway is a function of the initial insult to the cell. When SOD1 in PC12 cells is down-regulated to approximately 40% of its control levels, apoptosis occurs (Troy and Shelanski, 1994). This process appears to be mediated by peroxynitrite (Troy et al., 1996a), though the critical target of peroxynitrite in this model has not been identified. Cultured rat sympathetic neurons survive the down-regulation of SOD1 itself, but die rapidly when this treatment is coupled with the generation of nitric oxide. Down-regulation of SOD1 in PC12 cells is accompanied by an increase in the release of IL-1β suggesting the activation of an ICE-like enzyme (Troy et al., 1996b). In this case, death can be blocked by addition of anti-IL-1β or the IL-1 receptor antagonist (IL1-Ra) to the medium. Death of both PC12 and sympathetic neurons caused by SOD1 downregulation can also be blocked with a variety of inhibitors of the ICE-family of proteases (Troy et al., 1996b), but interestingly, not by the down-regulation of Nedd2. V-ANedd does not alter the release of IL-1, from V-ASOD1-treated cells. These data point strongly to the involvement of ICE itself or an ICE-like activity in this model of free-radical induced cell death and appear to exclude an obligatory role of Nedd2.

In contrast to the SOD1 down-regulation paradigm, antibodies to IL-1§ do not rescue PC12 cells and sympathetic neurons from serum and/or trophic factor withdrawal. Moreover, the ICE antagonist peptide ZYVAD-CMK, which effectively rescues the cells from down-regulation of SOD1, has negligible effects on death provoked by loss of trophic support (Troy et al., 1996b). However, down-regulation of Nedd2 in serum deprived naive PC12 cells and in NGF-deprived primed PC12 cells and sympathetic neurons rescues them from apoptotic death pointing to a requisite role of Nedd2 in this process.

The extracts show a major band at 53 kD, agreeing with the predicted molecular weight of Nedd2 (Kumar et al., 1994). There are also 3 minor bands which are detected by both antibodies, two of which are higher than the calculated molecular weight for Nedd2. Although the original report on Nedd2 reported that translation of the construct resulted in a major band of 53 kD and several minor bands of 45 and 19 kD (Kumar et al., 1994) the detection of higher molecular weight bands by antibodies against both the C- and N-termini of Nedd2 and their specific down-regulation by V-ANedd strongly suggests that they are Nedd2 products. These bands are also seen after in vitro transcription translation of rat Nedd2.

Previous studies have shown that overexpression of Nedd2 can induce apoptotic death and that an antisense construct can rescue cells from apoptosis (Kumar et al., 1994; Kumar, 1995). The studies of a specifically designed compound and its inhibition of trophic withdrawal mediated cell death presented here demonstrate directly that Nedd2 protein levels are down-regulated in neuronal cells by antisense treatment and, more significantly, that Nedd2 is required for neuronal cell death resulting from trophic factor withdrawal and not required when neuronal death is induced by SOD1 down-regulation. In addition, it is shown herein that Nedd2 is processed to a 36 kD cleavage product upon withdrawal of trophic support. Cleavage of Nedd2 has also been reported in another death paradigm (Srinivasan et al., 1996). ICE is proteolytically processed to an intermediate 35 kD peptide that is further cleaved to generate the active form, p20 (Thornberry et al., 1992; Yamin et al., 1996). The 36 kD Nedd2 cleavage product most likely represents such an intermediate form.

The results presented herein argue against the existence of a single "final common pathway" leading to apoptotic cell death. In the two paradigms presented here, trophic factor deprivation and SOD1 down-regulation, the general scheme is similar in that each pathway requires a cysteine aspartase but shows marked selectivity in the specific enzyme required. The differential association of specific cysteine aspartases with apoptosis evoked by different means may account for the proliferation of this family in vertebrates. The utilization of distinct cysteine aspartases by the same cells to promote death from different initiating stimuli raises the possibility that this selectivity can be exploited for the treatment of specific neurodegenerative disorders.

References

Batistatou A., Greene LA (1991). Aurintricarboxylic acid rescues PC12 cells and sympathetic neurons from cell death caused by nerve growth factor deprivation: correlation with suppression of endonuclease activity. J Cell Biol 115:461–471.

Brown Jr RH (1995) Amyotrophic lateral sclerosis: recent insights from genetics and transgenic mice. Cell 80:687–692.

Coyle JT, Puttfarcken P (1993) Oxidative stress, glutamate, and neurodegenerative disorders. Science 262:689–695.

Farinelli SE, Park DS, Greene LA (1996) Nitric oxide delays the death of trophic factor-deprived PC12 cells and sympathetic neurons by a cGMP-mediated mechanism. J. Neurosci. 16:2325–2334.

Fernandes-Alnemri T, Litwack G, Alnemri ES (1994) CPP32, a novel human apoptotic protein with homology to Caenorhabditis elegans cell death protein ced-3 and the mammalian IL-1§-converting enzyme J. Biol. Chem. 269:30761–30764.

Ferrari G, Greene LA (1994) Proliferative inhibition by dominant-negative Ras rescues naive and neuronally differentiated PC12 cells from apoptotic death. EMBO J 13:5922–5928.

Ferrari G, Yan CYI, Greene LA (1995) N-acetylcysteine (D- and L-stereoisomers) prevents apoptotic death of neuronal cells. J Neurosci 15:2857–2866.

Gagliardini V, Fernandez P-A, Lee RKK, Drexler HCA, Rotello RJ, Fishman MC, Yuan J. (1994) Prevention of vertebrate neuronal death by the crmA gene. Science 263:826–828.

Greene LA (1978) Nerve growth factor prevents the death and stimulates the neuronal differentiation of clonal PC12 pheochromocytoma cells in serum-free medium. J Cell Biol 78:744–755.

Greene LA, Tischler AS (1976). Establishment of a noradrenergic clonal line of rat adrenal pheochromocytoma cells which respond to nerve growth factor. Proc. Natl. Acad. Sci. U.S.A. 73, 2424–2428.

Hengartner MO, Ellis RE, Horvitz HR (1992) Caenorhabditis elegans gene ced-9 protects cells from programmed cell death. Nature. 356: 494–9

Kumar S (1995) Inhibition of apoptosis by the expression of antisense Nedd2. FEBS Letters 368:69–72. Kumar S, Knioshita M, Noda M, Copeland NG, Jenkins NA (1994) Induction of apoptosis by the mouse Nedd2 gene, which encodes a protein similar to the product of the Caenorhabditis elegans cell death gene ced-3 and the mammalian IL-1§-converting enzyme. Genes & Develop 8:1613–1626.

Lindenboim L, Haviv R, Stein R (1995) Inhibition of drug-induced apoptosis by survival factors in PC12 cells. J Neurochem 64:1054–1063.

Mesner PW, Winters TR, Green SH (1992) Nerve growth factor withdrawal-induced cell death in neuronal PC12 cells resembles that in sympathetic neurons. J Cell Biol 119:1669–1680.

Miura M, Zhu H, Rotello R, Hartweig EA, Yuan J (1994) Induction of apoptosis in fibroblasts by IL-1§-converting enzyme, a mammalian homolog of the c. elegans cell death gene ced-3. Cell 75:653–660.

Pittman RN, Wang S, DiBenedetto AJ, Mills JC (1993) A system for characterizing cellular and molecular events in programmed neuronal cell death. J Neurosci 13:3669–3680.

Rukenstein A, Rydel RE, Greene, LA (1991) Multiple agents rescue PC12 cells from serum-free cell death by translation- and transcription-independent mechanisms. J Neurosci 11:2552–2563.

Rydel RE, Greene LA (1988) cAMP analogs promote survival and neurite outgrowth in cultures of rat sympathetic and sensory neurons independently of nerve growth factor. Proc Natl Acad Sci USA 85:1257–1261.

Schapira AHV (1995) Oxidative stress in parkinson's disease. Neuropath and Appl Neurobiol 21:3–9.

Srinivasan A, Foster LM, Testa M-P, Ord T, Keane RW, Bredesen DE, Kayalar, C (1996) Bcl-2 expression in neural cells blocks activation of ICE.CED-3 family proteases during apoptosis. J Neurosci 16: 5654–5660.

Theodore L, Derossi D, Chassaing G, Llirbat B, Kubes M, Jordan P, Chneilweiss H, Godement P, Prochiantz A (1995) Intraneuronal delivery of protein kinase C pseudosubstrate leads to growth cone collapse. J Neurosci 15:7158–7167.

Thornberry NA, Bull HG, Calaycay JR, Chapman KT, Howard AD, Kostura MJ, Miller DK, Molineaux SM, Weidner JR, Aunins J, et al. (1992) A novel heterodimeric cysteine protease is required for interleukin-1 beta processing in monocytes. Nature. 356:768–74.

Troy CM, Brown K, Greene LA, and Shelanski ML (1990). Ontogeny of the neuronal intermediate filament protein, peripherin, in the mouse embryo. Neurosci. 36: 217–237.

Troy CM, Derossi D, Prochiantz A, Greene LA, Shelanski ML (1996a) Down-regulation of SOD1 leads to cell death by the NO-peroxynitrite pathway. J Neurosci 16:253–261.

Troy CM, Greene LA, Shelanski ML (1992). Neurite outgrowth in peripherin-depleted PC12 cells. J Cell Biol 117:1085–1092.

Troy CM, Shelanski ML (1994) Down-regulation of copper/zinc superoxide dismutase (SOD1) causes neuronal cell death. Proc. Natl. Acad. Sci. USA 91:6384–6387.

Troy CM, Stefanis L, Prochiantz A, Greene LA, Shelanski ML (1996b) The contrasting roles of ICE-family proteases and interleukin-1§ in apoptosis induced by trophic factor withdrawal and by SOD1 downregulation. Proc Natl Acad Sci USA 93: 5635–5640.

Troy CM, Stefanis L, Greene L A, Shelanski ML (1996c) Mechanisms of neuronal degeneration: a final common pathway? in Neuronal Regeneration, Reorganization and Repair F. Seil, ed. (New York, NY: Raven Press), pp. 103–112.

Wang L, Miura M, Bergeron L, Zhu H, Yuan J (1994) Ich-1, an Ice/ced-3-related gene, encodes both positive and negative regulators of programmed cell death. Cell 78: 739–750.

Williams LR (1995) Oxidative stress, age-related neurodegeneration, and the potential for neurotrophic. Cerebrovasc. Brain Metab. Rev. 7:55–73.

Yamin T-T, Ayala JM, Miller DK (1996) Activation of the native 45-kDa precursor form of interleukin-1-converting enzyme. J Biol Chem 271: 13273–13282.

Yuan J, Shahan S, Ledoux S, Ellis HM, Horvitz HR (1993) The c. elegans cell death gene ced-3 encodes a protein similar to mammalian interleukin-1β-converting enzyme. Cell 74: 641–652.

What is claimed is:

1. An oligonucleotide having the sequence 5'GCTCG-GCGCCGCCATTTCCAG3' (SEQ ID No. 1).

2. An oligonucleotide having the sequence 5'GTCAGCG-GCCATCAGCTT3' (Seq ID No. 2).

3. A composition comprising the oligonucleotide of claim 1 or 2, and an agent which directs the compound to a cell.

4. The composition of claim 3, wherein the agent comprises a portion of an Antennepedia polypeptide.

5. The composition of claim 3, wherein the agent comprises at least a portion of a polypeptide comprising the sequence NPyS-Arg-Gln-Ile-Lys-IleTrp-Phe-Gln-Asn-Arg-Arg-Met-Lys-Trp-Lys-Lys-(Seq. I.D. No. 3).

6. The composition of claim 3, wherein the agent comprises an antibody, an adjuvant or a cell-specific ligand.

7. The composition of claim 3, wherein the agent comprises PENETRATINI®.

8. The composition of claim 3, wherein the cell is a neuronal cell.

9. A composition comprising the oligonucleotide of claim 2 and a pharmaceutically acceptable carrier.

10. The composition of claim 9, wherein the carrier comprises a diluent, an appropriate adjuvant, a herpes virus, a liposome, a microencapsule, a neuronal cell receptor ligand, a neuronal-specific virus, a polymer encapsulated cell or a retroviral vector.

11. The composition of claim 9, wherein the pharmaceutically acceptable carrier is an aerosol, intravenous, oral or topical carrier.

12. A method of inhibiting trophic factor withdrawal mediated death of a cell which comprises contacting the cell in vitro with an amount of the composition of claim 3 effective to inhibit death of the cell.

13. The method of claim 12, wherein the cell is a human cell.

14. The method of claim 12, wherein the cell is a neuronal cell.

15. The method of claim 12 further comprising contracting the cell with an agent which directs the oligonucleotide to the cell.

16. The method of claim 15, wherein the agent comprises a polypeptide comprising at least a portion of an Antennapedia polypeptide.

17. The method of claim 15, wherein the agent comprises a polypeptide having the sequence NPyS-Arg-Gln-Ile-Lys-Ile-Trp-Phe-Gln-AsnArg-Arg-Met-Lys-Trp-Lys-Lys-(Seq. I.D. No. 3).

18. The method of claim 5, wherein the agent comprises an antibody, an adjuvant or a cell-specific ligand.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:1:

GCTCGGCGCC GCCATTTCCA G                                            21

(2) INFORMATION FOR SEQ ID NO:2:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:2:

GTCAGCGGCC ATCAGCTT                                                18

(2) INFORMATION FOR SEQ ID NO:3:

(i) SEQUENCE CHARACTERISTICS:
          (A) LENGTH: 16 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:3:

Arg Gln Ile Lys Ile Trp Phe Gln Asn Arg Arg Met Lys Trp Lys Lys
1               5                  10                  15

(2) INFORMATION FOR SEQ ID NO:4:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:4:

Arg Gln Ile Lys Ile Trp Phe Gln Asn Arg Arg Met Lys Trp Lys
1               5                  10                  15

(2) INFORMATION FOR SEQ ID NO:5:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: other nucleic acid -continued

```
    (xi) SEQUENCE DESCRIPTION: SEQ ID NO:5:

GCTCGGCGCC GCCATTTCCA G                                              21

(2) INFORMATION FOR SEQ ID NO:6:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Arg Gln Ile Lys Ile Trp Phe Gln Asn Arg Arg Met Lys Trp Lys Lys
1               5                   10                  15

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GTCAGCGGCC ATCAGCTT                                                  18
```